United States Patent [19]

Teshima et al.

[11] Patent Number: 4,778,757
[45] Date of Patent: Oct. 18, 1988

[54] METHOD FOR THE DETERMINATION OF SUBSTRATES OR ENZYME ACTIVITIES

[75] Inventors: Shinichi Teshima; Noboru Mitsuhida; Yoshitaka Nakagiri, all of Tsuruga, Japan

[73] Assignee: Toyo Boseki Kabushiki Kaisha, Osaka, Japan

[21] Appl. No.: 823,836

[22] Filed: Jan. 30, 1986

Related U.S. Application Data

[63] Continuation of Ser. No. 537,666, Sep. 30, 1983, abandoned.

[51] Int. Cl.$^4$ .............................................. C12Q 1/28
[52] U.S. Cl. ........................................ 435/28; 435/4; 435/11; 435/14; 435/15; 435/16; 435/18; 435/19; 435/22; 435/24; 435/25
[58] Field of Search .................. 435/11, 14, 15, 16, 435/18, 19, 22, 25, 28

[56] References Cited

U.S. PATENT DOCUMENTS

4,416,982 11/1983 Tsuda et al. ........................ 435/11

FOREIGN PATENT DOCUMENTS

0054358 11/1981 European Pat. Off. .

*Primary Examiner*—Sam Rosen
*Attorney, Agent, or Firm*—Wenderoth, Lind & Ponack

[57] ABSTRACT

There is provided an improved quantitative analysis for the determination of a substrate or enzyme. In the analysis for the enzyme, it is reacted with a known substrate and in the analysis for the substrate, it is reacted with a known enzyme and then the resultant substance is reacted with an oxidase to produce hydrogen peroxide which is then reacted with a peroxidase, phenol derivatie and coupler to form a colored material which is then subjected to colorimetic analysis. The improvement resides in conducting the foregoing process by adding to the test sample a first reagent containing the oxidase, peroxidase and phenol derivative represented by the formula:

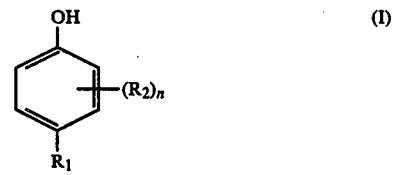

(I)

wherein $R_1$ is (a) a lower alkyl group having one to five carbon atoms or (b) the group defined in (a) above having a hydroxyl or sulfonic acid group, $R_2$ is a hydrogen or halogen atom, a lower alkyl group having one to five carbon atoms, a lower acyl group having one to five carbon atoms, a lower alkylether group having one to five carbon atoms, or a lower alkoxycarbonyl group having one to five carbon atoms, said groups being unsubstituted or substituted with a hydroxyl or sulfonic acid group, and n is 0 to 4. Then, there is added to the above mixture a second reagent containing the coupler and the enzyme.

5 Claims, No Drawings

METHOD FOR THE DETERMINATION OF SUBSTRATES OR ENZYME ACTIVITIES

This application is a continuation of application Ser. No. 537,666 filed Sept. 30, 1983 now abandoned.

The present invention relates to a method for the determination of substrates or enzyme activities in humor.

In a recent clinical assay for the determination of amounts of substrate or enzyme activities, a method is popularly employed in which an oxidase is reacted with a substrate or a substance produced by enzymatic reaction and the amount of produced hydrogen peroxide is measured.

In order to determine this hydrogen peroxide, a method is used in which (1) a coupler such as 4-aminoantipyrine, 3-methyl-2-benzthiazolinone hydrazine or the like is oxidation-condensed with (2) a chromogen such as phenol derivatives, aniline derivatives, naphthol derivatives or the like into a colored material by the enzymatic action of peroxidase, and then the optical absorbance of the material is measured. This method is characterized by the fact that operation is simple.

In recent years, however, in the clinical diagnosis of cholesterol esters, triglycerides, amylase, GOT, GPT, etc. using this measurement method, there is concern that an error is produced because free cholesterol, free glycerol, glucose, pyruvic acid, etc. in humor are concomitantly measured.

The present inventors extensively studies the problem with the object of preventing the concomitant measurement of free cholesterol, free glycerol, glucose, pyruvic acid, etc. in humor, thereby making an accurate determination of substrates such as cholesterol esters, triglycerides, etc., or the enzyme activities of amylase, glutamic-pyruvic transaminase (GPT), glutamic-oxaloacetic transaminase (GOT), etc., and thus attained the present invention. That is, according to the present invention substrates or enzyme activities in test samples are determined by reacting oxidase with a substrate or a substance produced by enzymatic reaction, and then measuring the produced hydrogen peroxide. The inventive feature resides in the use of a first liquid reagent containing (i) oxidase, (ii) peroxidase and (iii) a phenol derivative which is p-acetylphenol or is a phenol represented by the formula (I), described below and a second liquid reagent containing (iv) a coupler. After adding the first liquid reagent to a test sample, the second liquid reagent is added. Said phenol derivative (I) has the formula:

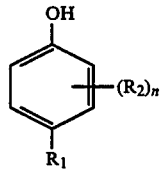

wherein $R_1$ is (a) a lower alkyl group having one to five carbon atoms or (b) the group defined in (a) above having a hydroxyl or sulfonic acid group, $R_2$ is a hydrogen or halogen atom, (1) a lower alkyl group having one to five carbon atoms, (2) a lower acyl group having one to five carbon atoms, (3) a lower alkylether group having one to five carbon atoms, (4) a lower alkoxycarbonyl group having one to five carbon, or (5) the groups defined in (1) to (4) above having a hydroxyl or sulfonic acid group, and n is 0 to 4.

In the present invention, by adding firstly the above first liquid reagent and then the second liquid reagent, it became possible to prevent the concomitant measurement of free cholesterol, free glycerol, glucose, pyruvic acid, etc. in humor, thereby making a simple and accurate determination of objective substrates or enzyme activities. In this case, it may be considered that hydrogen peroxide derived from the free cholesterol, free glycerol, glucose, pyruvic acid, etc. in humor is converted to a chemical substance showing no absorption in the visible region of the spectrum by reaction with phenol derivatives (self-condensation), and that this substance does not take part in the reaction system to measure the objective substrates or enzyme activities. Contrary to this, if the second liquid reagent is firstly added and then the first liquid reagent is added, the object is not achieved. The object is not also achieved in a case wherein a reagent containing coupler (ex. 4-aminoantipyrine) together with oxidase and peroxidase is employed as a first liquid reagent, a reagent containing a phenol derivative is taken as a second liquid reagent, and after adding the first liquid reagent, the second liquid reagent is added. For example, in the measurement of triglycerides, an attempt was made to colorimetrically determine the triglyceride alone by reacting coupler (ex. 4-aminoantipyrine) with hydrogen peroxide, as produced using glycerokinase and glycerophosphate oxidase (self-condensation), in the presence of peroxidase, and then adding lipase and a phenol derivative to form a colored material. In this method, however, the first reaction, i.e. reaction between 4-aminoantipyrine and hydrogen peroxide derived from free glycerol (self-condensation), produces a substance having an absorption in the visible region of the spectrum (a substance affecting the wavelength to be measured), thus producing a positive error in the colorimetric determination of the colored material produced by the second reaction.

Also, as a method to determine triglycerides alone, it is known to separately measure the total triglyceride value containing the concomitantly measured value of free glycerol and the value of the free glycerol alone and to obtain the triglyceride value as the difference between them. This method was, however, questionable in terms of simplicity. The present invention is superior in simplicity to the aforementioned method.

The method of the present invention is for determination substrates or enzyme activities in test samples by reacting a substrate or a substance produced by enzymatic reaction with oxidase and measuring the produced hydrogen peroxide.

The substrate to be determined includes cholesterol esters, triglycerides, creatinine, creatine, etc. contained in humor.

The enzyme to be determined includes aminotransaminases in humor such as glutamic-oxaloacetic transaminase (GOT), glutamiclpyruvic transaminase (GPT), amylase and the like.

As the substance produced by enzymatic reaction, there are mentioned, for example, cholesterol produced by reaction between cholesterol ester and cholesterol esterase, glycerol produced by reaction between triglyceride and lipase, glycerol-3-phosphate produced by reaction between glycerol and glycerokinase, pyruvic acid produced by reacting α-ketoglutaric acid and alanine with glutamic-pyruvic transaminase (GPT), glucose produced by reacting amylase or glucoamylase with starch or γ-cyclodextrin which is a substrate, and the like.

As the oxidase to be reacted with the aforementioned substrate or substance produced by enzymatic reaction, there are given for example cholesterol oxidase, glycerol oxidase, glycerophosphate oxidase, pyruvate oxidase, sarcosine oxidase, glucose oxidase and the like.

As the phenol derivative of the formula (I) used in the present invention, there are mentioned, for example, (a) p-cresol, p-ethylphenol, 4-n-propylphenol, p-isopropylphenol, o-chloro-p-cresol, m-chloro-p-cresol, 2,4-dimethylphenol, 3,4-diethylphenol, 2,4,6-trimethylphenol, m-hydroxymethyl-p-cresol, 3-sulfopropyl-4-ethylphenol and the like, and (b) p-hydroxymethylphenol, p-hydroxyethylphenol, p-sulfoxymethylphenol, p-sulfoxyethylphenol, 3-chloro-4-hydroxymethylphenol, 2-methyl-4-hydroxymethylphenol, 3,4-dihydroxymethylphenol, 2-acetyl-4-hydroxymethylphenol, 3-methoxy-4-hydroxymethylphenol, 3-methoxycarbonyl-4-hydroxymethylphenol and the like.

The coupler used in the present invention includes for example 4-aminoantipyrine, 3-methyl-2-benzthiazole hydrazone and the like.

The reagent used in the present invention includes a first liquid reagent which is a reagent containing (i) oxidase, (ii) peroxidase and (iii) a phenol derivative, and a second liquid reagent which is a reagent containing (iv) a coupler. The second liquid reagent may contain an anilin derivative.

As the aniline derivative, there are mentioned, for example, aniline, N,N-dimethylaniline, N,N-diethylaniline, N,N-diethyl-m-toluidine, N,N-dimethyl-m-anisidine, N-ethyl-N-(3-methylphenyl)-N'-acetylethylenediamine, N-ethyl-N-(β-hydroxyethyl)-m-toluidine, N-ethyl-N-(2-hydroxy-3-sulfopropyl)-m-toluidine, N-ethyl-N-sulfopropyl-m-toluidine, N-ethyl-N-sulfopropyl-3,5-dimethoxyaniline, N-ethyl-N-(2-hydroxy-3-sulfopropyl)-3,5-dimethoxyaniline, N-ethyl-N-sulfopropyl-m-anisidine, N-ethyl-N-(2-hydroxy-3-sulfopropyl)-m-anisidine and the like.

The first and second liquid reagents may contain, in addition to the foregoing components, a buffer and if necessary, a surface active agent, a stabilizer and the like. As the buffer, common ones may be used, and the pH of the first and second liquid reagents is preferably adjusted to generally 5 to 10.

The content of phenol derivative of the first liquid reagent is $1 \times 10^{-5}$ to $1 \times 10^{-2}$M, and that of the coupler of the second one is $1 \times 10^{-6}$ to $1 \times 10^{-2}$M.

The reagents used in the present invention may contain other enzymes or substrates, various stabilizers, reagents for the removal of interfering substances, surface active agents and the like.

Next, the substrate or enzyme activity will be explained specifically. But, the present invention is not to be interpreted as being limited to those specifically explained here.

For the determination of a substrate, for example cholesterol ester, there are prepared the first liquid reagent which is a reagent containing cholesterol oxidase, peroxidase, a phenol derivative and a buffer, and the second liquid reagent which is a reagent containing cholesterol esterase, 4-aminoantipyrine and a buffer. The test sample is reacted with the first liquid reagent, whereby hydrogen peroxide of free cholesterol origin is reacted with the phenol derivative in the presence of peroxidase (self-condensation). Thereafter, the second liquid reagent is added, whereby hydrogen peroxide, as produced from cholesterol of cholesterol ester origin, is reacted with the phenol derivative and 4-aminoantipyrine in the presence of peroxidase to obtain a color material. The colored material is then colorimetrically determined.

For the determination of a substrate, for example triglyceride, there are prepared the first liquid reagent which is a reagent containing glycerol oxidase, peroxidase, a phenol derivative and a buffer or a reagent containing glycerol kinase, glycerophosphate oxidase, peroxidase, a phenol derivative and a buffer, and the second liquid reagent which is a reagent containing lipoprotein lipase, 4-aminoantipyrine and a buffer. The test sample is reacted with the first liquid reagent, whereby hydrogen peroxide of free glycerol origin is reacted with the phenol derivative in the presence of peroxidase (self-condensation). Thereafter, the second liquid reagent is added, whereby hydrogen peroxide produced from glycerol of triglyceride origin is colorimetrically determined.

For the determination of the activity of an enzyme, for example glutamic-pyruvic transaminase (GPT), there are prepared the first liquid reagent which is a reagent containing pyruvate oxidase, peroxidase, a phenol derivative and a buffer, and the second liquid reagent which is a reagent containing α-ketoglutaric acid, DL-alanine, 4-aminoantipyrine and a buffer. The test sample is reacted with the first liquid reagent, whereby hydrogen peroxide of free pyruvic acid origin is reacted with the phenol derivative in the presence of peroxidase (self-condensation). Thereafter, the second liquid reagent is added, whereby hydrogen peroxide having its origin in pyruvic acid produced by the action of GPT is colorimetrically determined.

The method of the present invention may also be applied to the determination of hydrogen peroxide with other oxidases, in addition to the foregoing determination of substrates and enzyme activities.

The method of the present invention, as compared with the determination method using a mixture of the first liquid reagent and the second one, makes it possible to decrease the concomitant measurement of a substance which coexists in test samples and produces a measurement error, thereby simplifying the determination of objective substrates or enzyme activities.

Next, the present invention will be illustrated with reference to the following examples.

EXAMPLE 1

Triglyceride in the samples was determined by the method described below using the reagents described below:

1. Sample

| | |
|---|---|
| Glycerin (26 mg/dl) solution | (1) |
| Glycerin (52 mg/dl) solution | (2) |
| Glycerin (104 mg/dl) solution | (3) |
| Serum a:water = 9:1 | (4) |
| Serum a:aqueous glycerin solution (1,040 mg/dl) = 9:1 | (5) |
| Serum b:water = 9:1 | (6) |
| Serum b:aqueous glycerin solution (1,040 mg/dl) = 9:1 | (7) |

2. Reagent

The reagents A and a to e were prepared, and a phenol derivative contained in each reagent is as shown in Table 1.

First liquid reagent:

| Tris buffer (pH 7.0) | |
| --- | --- |
| Glycerokinase | 2.0 unit/ml |
| Glycerophosphate oxidase | 6.0 unit/ml |
| Peroxidase | 10.0 unit/ml |
| Phenol derivative | 5 mg/dl |

Second liquid reagent:

| Tris buffer (pH 7.0) | |
| --- | --- |
| Lipoprotein lipase | 600 unit/ml |
| 4-Aminoantipyrine | 10 mg/dl |
| N—ethyl-N—(3-sulfopropyl)-m-anisidine | 90 mg/dl |

TABLE 1

| | Reagent | Phenol derivative |
| --- | --- | --- |
| Present invention | A | p-Cresol |
| Comparative example | a | None |
| | b | Phenol |
| | c | m-Bromophenol |
| | d | p-Chlorophenol |
| | e | 2,4-Dichlorophenol |

3. Measurement method

To 20 μl of each sample was added 2 ml of the first liquid reagent to carry out the reaction at 37° C. for 5 minutes. Thereafter, 1 ml of the second liquid reagent was added to carry out reagent at 37° C. for 10 minutes. A colored material produced from 4-aminoantipyrine and N-ethyl-N-(3-sulfopropyl)-m-anisidine was measured for absorbance at a wavelength of 540 nm. The result is shown in Table 2.

TABLE 2

| | | Sample | | | | | | |
| --- | --- | --- | --- | --- | --- | --- | --- | --- |
| Reagent | Distilled water | ① | ② | ③ | ④ | ⑤ | ⑥ | ⑦ |
| A | 0.008 | 0.008 | 0.008 | 0.008 | 0.345 | 0.346 | 0.091 | 0.091 |
| a | 0.008 | 0.233 | 0.482 | 0.963 | 0.343 | 1.290 | 0.089 | 1.034 |
| b | 0.008 | 0.020 | 0.032 | 0.049 | 0.342 | 0.384 | 0.091 | 0.135 |
| c | 0.008 | 0.020 | 0.032 | 0.048 | 0.343 | 0.381 | 0.089 | 0.131 |
| d | 0.007 | 0.021 | 0.034 | 0.051 | 0.341 | 0.390 | 0.088 | 0.135 |
| e | 0.008 | 0.025 | 0.042 | 0.074 | 0.344 | 0.411 | 0.089 | 0.157 |

In Table 2, distilled water is a control to the samples ①, ② and ③, and the samples ④ and ⑥ are a control to the samples ⑤ and ⑦, respectively.

It can be seen from this result that p-cresol, as used in the reagent A, is superior in glycerol-eliminating ability to m-bromophenol, p-chlorophenol, phenol and 2,4-dichlorophenol used in other reagents.

EXAMPLE 2

Triglyceride in the samples was determined by the method described below using the reagents described below:

1. Sample

| Glycerin (26 mg/dl) solution | ① |
| --- | --- |
| Glycerin (52 mg/dl) solution | ② |
| Glycerin (104 mg/dl) solution | ③ |
| Serum a:water = 9:1 | ④ |
| Serum a:aqueous glycerin solution (1,040 mg/dl) = 9:1 | ⑤ |
| Serum b:water = 9:1 | ⑥ |
| Serum b:aqueous glycerin solution (1,040 mg/dl) = 9:1 | ⑦ |

2. Reagent

The reagents A to C and a to e were prepared, and a phenol derivative contained in each reagent is as shown in Table 3.

First liquid reagent:

| Tris buffer (pH 7.0) | |
| --- | --- |
| Glycerokinase | 2.0 unit/ml |
| Glycerophosphate oxidase | 6.0 unit/ml |
| Peroxidase | 10.0 unit/ml |
| Phenol derivative | 5 mg/dl |

Second liquid reagent:

| Tris buffer (pH 7.0) | |
| --- | --- |
| Lipoprotein lipase | 600 unit/ml |
| 4-Aminoantipyrine | 10 mg/dl |
| N,N—diethyl-m-toluidine | 90 mg/dl |

TABLE 3

| | Reagent | Phenol derivative |
| --- | --- | --- |
| Present invention | A | p-Ethylphenol |
| | B | p-Sulfoxymethylphenol |
| | C | p-Hydroxymethylphenol |
| Comparative example | a | None |
| | b | o-Chlorophenol |
| | c | 3,5-Dimethoxyphenol |
| | d | o-Isopropylphenol |
| | e | 2,6-Dimethoxyphenol |

3. Measurement method

To 20 μl of each sample was added 2 ml of the first liquid reagent to carry out reaction at 37° C. for 5 minutes. Thereafter, 1 ml of the second liquid reagent was added to carry out reaction at 37° C. for 10 minutes. A colored material produced for 4-aminoantipyrine and N,N-diethyl-m-toluidine was measured for absorbance at a wavelength of 540 nm. The result is shown in Table 4.

TABLE 4

| | Distilled water | ① | ② | ③ | ④ | ⑤ | ⑥ | ⑦ |
| --- | --- | --- | --- | --- | --- | --- | --- | --- |
| A | 0.008 | 0.008 | 0.008 | 0.009 | 0.375 | 0.373 | 0.124 | 0.124 |
| B | 0.008 | 0.008 | 0.009 | 0.010 | 0.374 | 0.377 | 0.122 | 0.125 |
| C | 0.008 | 0.009 | 0.010 | 0.011 | 0.375 | 0.378 | 0.123 | 0.126 |
| a | 0.008 | 0.260 | 0.518 | 1.040 | 0.371 | 1.411 | 0.120 | 1.150 |
| b | 0.008 | 0.023 | 0.033 | 0.050 | 0.370 | 0.423 | 0.124 | 0.167 |
| c | 0.008 | 0.018 | 0.028 | 0.040 | 0.372 | 0.404 | 0.123 | 0.156 |
| d | 0.007 | 0.017 | 0.029 | 0.051 | 0.373 | 0.418 | 0.122 | 0.167 |
| e | 0.008 | 0.025 | 0.082 | 0.158 | 0.375 | 0.528 | 0.125 | 0.277 |

It can be seen from this result that p-ethylphenol, p-sulfoxymethylphenol and p-hydroxymethylphenol, as used in the reagents A, B and C, respectively, are superior in glycerol-eliminating ability to o-chlorophenol, 3,5-dimethoxyphenol, o-isopropylphenol and 2,6-dimethoxyphenol used in other reagents.

EXAMPLE 3

Glutamic-pyruvic transaminase (GPT) in the samples was determined by the method described below using the reagents described below:

1. Sample

| | |
|---|---|
| Pyruvic acid (25 mg/dl) solution | ① |
| Pyruvic acid (50 mg/dl) solution | ② |
| Pyruvic acid (100 mg/dl) solution | ③ |
| Serum a:water = 9:1 | ④ |
| Serum a:pyruvic acid (1000 mg/dl) = 9:1 | ⑤ |
| Serum b:water = 9:1 | ⑥ |
| Serum b:pyruvic acid (1000 mg/dl) = 9:1 | ⑦ |

2. Reagent

The reagents A to C and a to e were prepared, and a phenol derivative contained in each reagent is as shown in Table 5.

First liquid reagent:

| Phosphate buffer (pH 7.0) | |
|---|---|
| Pyruvate oxidase | 6 unit/ml |
| Peroxidase | 10.0 unit/ml |
| Thiamin pyrophosphate | 0.045% |
| Flavin adenine dinucleotide | 0.002% |
| Phenol derivative | 5 mg/dl |
| Magnesium acetate | 0.007 M |

Second liquid reagent:

| Phosphate buffer (pH 7.0) | |
|---|---|
| α-Ketoglutaric acid | 0.035 M |
| DL-alanine | 0.7 M |
| 4-Aminoantipyrine | 2 mg/dl |
| N—ethyl-N—(3-sulfopropyl)-m-anisidine | 20 mg/dl |

Reaction stopper:

| Phosphate buffer (pH 7.0) | |
|---|---|
| Disodium ethylenediamine tetraacetate | 0.05 M |
| Trisodium citrate | 0.1 M |

TABLE 5

| | Reagent | Phenol derivative |
|---|---|---|
| Present invention | A | p-Cresol |
| | B | p-ethylphenol |
| | C | p-Acetylphenol |
| Comparative example | a | None |
| | b | Phenol |
| | c | m-Chlorophenol |
| | d | p-Bromophenol |
| | e | 2,4-Dibromophenol |

3. Measurement method

To 20 μl of each sample was added 2 ml of the first liquid reagent to carry out reaction at 37° C. for 5 minutes. Thereafter, 1 ml of the second liquid reagent was added to carry out reaction at 37° C. for 10 minutes. A colored material produced from 4-aminoantipyrine and N-ethyl-N-(3-sulfopropyl)-m-anisidine was measured for absorbance at a wavelength of 540 nm. The result is shown in Table 6.

TABLE 6

| Reagent | Distilled water | ① | ② | ③ | ④ | ⑤ | ⑥ | ⑦ |
|---|---|---|---|---|---|---|---|---|
| A | 0.009 | 0.009 | 0.009 | 0.009 | 0.051 | 0.051 | 0.154 | 0.153 |
| B | 0.010 | 0.010 | 0.010 | 0.010 | 0.052 | 0.052 | 0.152 | 0.153 |
| C | 0.009 | 0.010 | 0.010 | 0.010 | 0.051 | 0.048 | 0.152 | 0.147 |
| a | 0.009 | 0.228 | 0.467 | 0.951 | 0.049 | 0.989 | 0.151 | 1.097 |
| b | 0.010 | 0.022 | 0.030 | 0.047 | 0.050 | 0.093 | 0.153 | 0.201 |
| c | 0.010 | 0.022 | 0.033 | 0.045 | 0.050 | 0.091 | 0.154 | 0.199 |
| d | 0.010 | 0.020 | 0.035 | 0.052 | 0.051 | 0.098 | 0.153 | 0.210 |
| e | 0.009 | 0.025 | 0.041 | 0.076 | 0.052 | 0.103 | 0.152 | 0.221 |

It can be seen from this result that p-cresol, p-ethylphenol and p-acetylphenol, as used in the reagents A, B and C, respectively, are superior in pyruvic acid-eliminating ability to phenol, m-chlorophenol, p-bromophenol and 2,4-dibromophenol used in other reagents.

EXAMPLE 4

Cholesterol ester in the samples was determined by the method described below using the reagents described below:

1. Sample

| | |
|---|---|
| Cholesterol (50 mg/dl) solution | ① |
| Cholesterol (100 mg/dl) solution | ② |
| Cholesterol (500 mg/dl) solution | ③ |
| Serum a:water = 9:1 | ④ |
| Serum a:aqueous cholesterol solution (5,000 mg/dl) = 9:1 | ⑤ |
| Serum b:water = 9:1 | ⑥ |
| Serum b:aqueous cholesterol solution (5,000 mg/dl) = 9:1 | ⑦ |

2. Reagent

The reagents A to C and a to d were prepared, and a phenol derivative contained in each reagent is as shown in Table 7.

First liquid reagent:

| Phosphate buffer (pH 5.35) | |
|---|---|
| Cholesterol oxidase | 0.8 unit/ml |
| Peroxidase | 10 unit/ml |
| Phenol derivative | 5 mg/dl |

Second liquid reagent:

| Phosphate buffer (pH 5.35) | |
|---|---|
| Cholesterol esterase | 0.4 unit/ml |
| 4-Aminoantipyrine | 2 mg/dl |
| N,N—dimethyl-m-anisidine | 20 mg/dl |

TABLE 7

| | Reagent | Phenol derivative |
|---|---|---|
| Present invention | A | p-Cresol |
| | B | p-Ethylphenol |
| | C | p-Acetylphenol |
| Comparative example | a | None |
| | b | o-Bromophenol |
| | c | 3,4-Dimethoxyphenol |
| | d | o-Isopropylphenol |

3. Measurement method

To 20 μl of each sample was added 2 ml of the first liquid reagent to carry out reaction at 37° C. for 5 minutes. Thereafter, 1 ml of the second liquid reagent was added to carry out reaction at 37° C. for 10 minutes. A colored material produced from 4-aminoantipyrine and N,N-diethyl-m-anisidine was measured for absorbance at a wavelength of 535 nm. The result is shown in Table 8.

TABLE 8

| | Distilled water | ① | ② | ③ | ④ | ⑤ | ⑥ | ⑦ |
|---|---|---|---|---|---|---|---|---|
| A | 0.008 | 0.008 | 0.008 | 0.008 | 0.218 | 0.218 | 0.564 | 0.564 |
| B | 0.008 | 0.008 | 0.008 | 0.008 | 0.217 | 0.216 | 0.563 | 0.564 |
| C | 0.008 | 0.008 | 0.008 | 0.008 | 0.216 | 0.210 | 0.564 | 0.559 |
| a | 0.008 | 0.126 | 0.260 | 1.209 | 0.217 | 1.401 | 0.563 | 1.714 |
| b | 0.008 | 0.032 | 0.041 | 0.063 | 0.218 | 0.271 | 0.564 | 0.629 |
| c | 0.007 | 0.035 | 0.047 | 0.069 | 0.217 | 0.280 | 0.564 | 0.629 |
| d | 0.008 | 0.040 | 0.052 | 0.072 | 0.218 | 0.270 | 0.564 | 0.640 |

It can be seen from this result that p-cresol, p-ethylphenol and p-acetylphenol, as used in the reagents A, B and C, respectively, are superior in cholesterol-eliminating ability to o-bromophenol, 3,4-dimethoxyphenol and o-isopropylphenol used in other reagents.

EXAMPLE 5

Triglyceride in the samples was determined by the method described below using the reagents described below:

1. Sample

| | |
|---|---|
| Glycerin (26 mg/dl) solution | ① |
| Glycerin (52 mg/dl) solution | ② |
| Glycerin (104 mg/dl) solution | ③ |
| Serum a:water = 9:1 | ④ |
| Serum a:aqueous glycerin solution (1,040 mg/dl) = 9:1 | ⑤ |
| Serum b:water = 9:1 | ⑥ |
| Serum b:aqueous glycerin solution (1,040 mg/dl) = 9:1 | ⑦ |

2. Reagent

The reagents A to C and a to e were prepared, and a phenol derivative or aniline derivative contained in each reagent is as shown in Table 9.

First liquid reagent:

| Tris buffer (pH 7.0) | |
|---|---|
| Glycerokinase | 2.0 unit/ml |
| Glycerophosphate oxidase | 6.0 unit/ml |
| Peroxidase | 10.0 unit/ml |
| Phenol derivative or aniline derivative | 5 mg/dl |

Second liquid reagent:

| Tris buffer (pH 7.0) | |
|---|---|
| Lipoprotein lipase | 600 unit/ml |
| 4-Aminoantipyrine | 10 mg/dl |
| N,N—diethyl-m-toluidine | 90 mg/dl |

TABLE 9

| | Reagent | Phenol derivative or aniline derivative |
|---|---|---|
| Present invention | A | p-Cresol |
| | B | p-Ethylphenol |
| | C | p-Acetylphenol |
| Comparative example | a | None |
| | b | Methyl p-oxybenzoate |
| | c | N—ethyl-N—(3-sulfopropyl)-m-anisidine |
| | d | N,N—dimethylanisidine |

TABLE 9-continued

| Reagent | Phenol derivative or aniline derivative |
|---|---|
| e | N,N—diethylaniline |

3. Measurement method

To 20 μl of each samples was added 2 ml of the first liquid reagent to carry out reaction at 37° C. for 5 minutes. Thereafter, 1 ml of the second liquid reagent was added to carry out reaction at 37° C. for 10 minutes. A colored material produced from 4-aminoantipyrine and N,N-diethyl-m-toluidine was measured for absorbance at a wavelength of 540 nm. The result is shown in Table 10.

TABLE 10

| | Distilled water | ① | ② | ③ | ④ | ⑤ | ⑥ | ⑦ |
|---|---|---|---|---|---|---|---|---|
| A | 0.008 | 0.008 | 0.008 | 0.008 | 0.254 | 0.255 | 0.124 | 0.124 |
| B | 0.008 | 0.008 | 0.008 | 0.008 | 0.254 | 0.254 | 0.123 | 0.123 |
| C | 0.008 | 0.008 | 0.008 | 0.008 | 0.253 | 0.248 | 0.122 | 0.118 |
| a | 0.008 | 0.261 | 0.517 | 1.040 | 0.253 | 1.273 | 0.123 | 1.299 |
| b | 0.007 | 0.008 | 0.008 | 0.008 | 0.254 | 0.239 | 0.124 | 0.109 |
| c | 0.008 | 0.010 | 0.011 | 0.014 | 0.255 | 0.273 | 0.123 | 0.150 |
| d | 0.008 | 0.021 | 0.039 | 0.051 | 0.253 | 0.296 | 0.124 | 0.171 |
| e | 0.008 | 0.010 | 0.012 | 0.016 | 0.254 | 0.283 | 0.123 | 0.165 |

It can be seen from this result that p-cresol, p-ethylphenol and p-acetylphenol, as used in the reagents A, B and C, respectively, are superior in the glycerol-eliminating ability to methyl p-oxybenzoate, N-ethyl-N-(3-sulfopropyl)-m-anisidine, N,N-dimethylanisidine and N,N-diethylaniline used in other reagents.

What is claimed is:

1. In a method for the quantitative determination of a substrate in a test sample which comprises the steps of:
   (a) reacting the substrate in the test sample with an enzyme to produce a substance capable of forming hydrogen peroxide upon reaction with an oxidase,
   (b) reacting said substrate with an oxidase to form hydrogen peroxide,
   (c) reacting the hydrogen peroxide thus produced with a phenol derivative and coupler in the presence of a peroxidase to form a colored material, and
   (d) subjecting said colored material to colorimetric analysis to determine the amount of said substrate in said test sample,
   the improvement which comprises conducting the foregoing method as follows:
   ($a^1$) adding to the test sample a first reagent containing:
      (i) said oxidase
      (ii) said peroxidase, and
      (iii) said phenol derivative, which phenol derivative is p-acetylphenol or a phenol represented by the following formula:

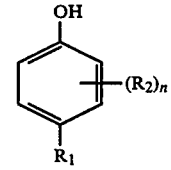

(I)

wherein $R_1$ is (a) a lower alkyl group having one to five carbon atoms or (b) the group defined in (a) above having a hydroxyl or sulfonic acid group, $R_2$ is a hydrogen or halogen atom, a lower alkyl group having one to five carbon atoms, a lower acyl group having one to five carbon atoms, a lower alkylether group having one to five carbon atoms, or a lower alkoxycarbonyl group having one to five carbon atoms, said groups being unsubstituted or substituted with a hydroxyl or sulfonic acid group, and n is 0 to 4, (b¹) adding to the product of a¹) a second reagent containing:
(iv) said coupler and
(v) said enzyme to form a colored material, and (c¹) subjecting said colored material to colorimetric analysis.

2. The method as claimed in claim 1 wherein the substrate in the test sample is triglyceride, the first reagent further contains glycerokinase, the oxidase is glycerophosphate oxidase and the enzyme in the second reagent is lipoprotein lipase.

3. The method of claim 1 wherein the substrate is a cholesterol ester, triglyceride, creatinine or creatine.

4. In a method for the quantitative determination of an enzyme in a test sample which comprises the steps of:
(a) reacting the enzyme in the test sample with a substrate to produce a substance capable of forming hydrogen peroxide upon reaction with an oxidase,
(b) reacting said substance with an oxidase to form hydrogen peroxide,
(c) reacting the hydrogen peroxide thus produced with a phenol derivative and coupler in the presence of a peroxidase to form a colored material, and
(d) subjecting said colored material to colorimetric analysis to determine the amount of said substrate in said test sample, the improvement which comprises conducting the foregoing method as follows:
(a¹) adding to the test sample a first reagent containing:
(i) said oxidase
(ii) said peroxidase, and
(iii) said phenol derivative, which phenol derivative is p-acetylphenol or a phenol represented by the following formula:

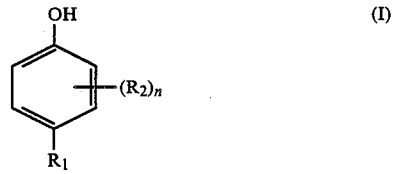

wherein $R_1$ is (a) a lower alkyl group having one to five carbon atoms or (b) the group defined in (a) above having a hydroxyl or sulfonic acid group, $R_2$ is a hydrogen or halogen atom, a lower alkyl group having one to five carbon atoms, a lower acyl group having one to five carbon atoms, a lower alkylether group havng one to five carbon atoms, or a lower alkoxycarbonyl group having one to five carbon atoms, said groups being unsubstituted or substituted with a hydroxyl or sulfonic acid group, and n is 0 to 4, (b¹) according to the product of (a¹) a second reagent containing:
(iv) said coupler and
(v) said enzyme to form a colored material, and (c¹) subjecting said colored material to colorimetric analysis.

5. The method of claim 4 wherein the enzyme is glutamicoxaloacetic transaminase, glutamic-pyruvic transaminase, or amylase.

* * * * *